United States Patent
Rosborough et al.

(10) Patent No.: US 6,298,267 B1
(45) Date of Patent: Oct. 2, 2001

(54) METHOD AND APPARATUS FOR TREATMENT OF CARDIAC ELECTROMECHANICAL DISSOCIATION

(75) Inventors: John P. Rosborough, Houston, TX (US); D. Curtis Deno, Andover, MN (US); Lawrence J. Stotts, Lake Jackson, TX (US)

(73) Assignee: Intermedics Inc., Angleton, TX (US)

( * ) Notice: Subject to any disclaimer, the term of this patent is extended or adjusted under 35 U.S.C. 154(b) by 0 days.

(21) Appl. No.: 09/520,858

(22) Filed: Mar. 7, 2000

Related U.S. Application Data (63) Continuation-in-part of application No. 09/303,380, filed on Apr. 30, 1999.

(51) Int. Cl.[7] .................................................. A61N 1/39
(52) U.S. Cl. ................................................................ 607/6
(58) Field of Search ..................................... 607/4–6, 14

(56) References Cited

U.S. PATENT DOCUMENTS

| | | | |
|---|---|---|---|
| 3,815,611 | 6/1974 | Denniston, III | 128/419 D |
| 4,303,075 | 12/1981 | Heilman et al. | 128/419 PG |
| 4,404,972 | 9/1983 | Gordon et al. | 128/419 PG |
| 4,800,883 | 1/1989 | Winstrom | 128/419 D |
| 4,880,005 | 11/1989 | Pless et al. | 128/419 PG |
| 4,904,472 | 2/1990 | Belardinelli et al. | 514/263 |
| 4,980,379 | 12/1990 | Belardinelli et al. | 514/821 |

(List continued on next page.)

OTHER PUBLICATIONS

*Advanced Cardiac Life Support*, American Heart Association, pp. 1–10 to 1–28 and 17–1 to 17–10, (1997–99).

Bocka, J.J., et al., "Electromechanical Dissociation in Human Beings: An Echocardiographic Evaluation", *Annals of Emergency Medicine*, 17(5), pp. 450–452, (May 1988).

Cripps, T., et al., "The Management of Electromechanical Dissociation", *Resuscitation*, 22 (2), pp. 173–180, (1991).

(List continued on next page.)

Primary Examiner—William E. Kamm
(74) Attorney, Agent, or Firm—Schwegman, Lundberg, Woessner & Kluth, P.A.

(57) ABSTRACT

An apparatus and method for treating post-defibrillation electromechanical dissociation ("EMD") or pulseless electrical activity ("PEA"). A first embodiment comprises an implantable defibrillator with the capability of detecting and treating post defibrillation EMD. The stimulator/defibrillator has one or more leads with electrodes and at least one electrode for defibrillation. A sense circuit senses the electrical condition of the heart of the patient. A second sensor senses a parameter correlated to the state of blood flow. The cardiac stimulator/defibrillator detects and terminates ventricular tachyarrhythmia or fibrillation. If the stimulator/defibrillator detects the presence of electrical rhythm in the heart correlated, however, with inadequate blood flow to sustain life (EMD), the device provides an output to stimulate the heart to overcome EMD. The device may also be an external defibrillator. The method for treating the heart to restore blood flow where electromechanical dissociation occurs after termination of a ventricular tachyarrhythmia or ventricular fibrillation comprises identifying electromechanical disassociation after termination of a ventricular tachyarrhythmia or a fibrillation and inducing or re-inducing ventricular fibrillation and subsequently applying defibrillating shocks to terminate the fibrillation.

36 Claims, 7 Drawing Sheets

U.S. PATENT DOCUMENTS

| | | | |
|---|---|---|---|
| 5,002,052 | 3/1991 | Haluska | 128/419 PG |
| 5,215,083 | 6/1993 | Drane et al. | 128/419 D |
| 5,305,745 | 4/1994 | Zacouto | 128/637 |
| 5,383,912 | 1/1995 | Cox et al. | 607/32 |
| 5,405,362 | 4/1995 | Kramer et al. | 607/5 |
| 5,476,484 | 12/1995 | Hedberg | 607/23 |
| 5,480,412 | 1/1996 | Mouchawar et al. | 607/6 |
| 5,480,413 | 1/1996 | Greenhut et al. | 607/14 |
| 5,496,361 | 3/1996 | Moberg et al. | 607/122 |
| 5,628,777 | 5/1997 | Moberg et al. | 607/122 |
| 5,713,935 | 2/1998 | Prutchi et al. | 607/28 |
| 5,782,879 | 7/1998 | Rosborough et al. | 607/6 |
| 5,792,183 | 8/1998 | Esler | 607/4 |
| 5,799,350 | 9/1998 | Ferek-Petric et al. | 607/17 |
| 5,935,158 | 8/1999 | Holmstrom et al. | 607/116 |
| 5,999,850 | 12/1999 | Dawson et al. | 607/4 |
| 6,009,349 | 12/1999 | Mouchawar et al. | 607/6 |
| 6,057,137 | 5/2000 | Tranquillo et al. | 435/174 |

OTHER PUBLICATIONS

Grubman, E.M., et al., "Cardiac Death and Stored Eletrograms in Patients With Third–Generation Implantable Cardioverter–Defibrillators", *Journal of the American College of Cardiology*, 32 (4), pp. 1056–1062, (Oct. 1998).

METHOD AND APPARATUS FOR TREATMENT OF CARDIAC ELECTROMECHANICAL DISSOCIATION

This is a continuation-in-part of U.S. patent application Ser. No. 09/303,380, filed Apr. 30. 1999. The disclosure of that application is incorporated herein by reference in its entirety.

FIELD OF OUR INVENTION

Our invention is directed towards a method for treating cardiac dysfunction arising from postdefibrillation electromechanical dissociation and to an apparatus for providing such treatment. In particular, the invention also relates to an implantable cardiac cardiovertor-defibrillator, capable of detecting fibrillation, delivering a defibrillating shock, sensing electrical cardiac rhythmicity coupled with inadequate blood flow and delivering a therapy to restore cardiac function.

BACKGROUND OF OUR INVENTION

Electromechanical dissociation (EMD) is a clinical condition of cardiac arrest with no palpable pulse or blood flow although coordinated ventricular electrical activity exists. This does not exclude the possibility of very weak ventricular contractions, not usually perceptible by standard external or indirect clinical means, which do not produce significant perfusion pressure capable of sustaining life. More recently, the name "Pulseless Electrical Activity" (PEA) has been used for this condition, which may be more descriptive. Since the late 1980's, clinical studies have found a significant number of patients who were judged to be experiencing EMD, but who also had very weak but coordinated mechanical contractions. Some investigators have become dissatisfied with an early definition of EMD as "organized electrical depolarization of the heart without synchronous myocardial fiber shortening and therefore without cardiac output." See, for example, Bocka, J J, et al., *Electromechanical dissociation in human beings: An echocardiographical evaluation,* Annals of Emergency Medicine, 17:450–452, 1988. "PEA" may therefore better describe a clinical presentation of a cardiac rhythm compatible with adequate perfusion, but producing undetectable or grossly inadequate pulse pressures. For our purposes, however, we will use EMD or electromechanical dissociation to also refer to conditions which are now sometimes called PEA or pulseless electrical activity.

EMD may occur after defibrillation or as the primary modality of cardiac arrest, distinct from fibrillation. Where EMD occurs, the prognosis for recovery is very poor, with survival rates reported on the order of a few percent. When persistent and untreated, EMD is associated with global ischemia, which will result in rapidly progressive and irreversible brain damage within minutes. In the past, the accepted remedy has been to provide continued life-support while waiting for cardiac output to return. Life support measures commonly include CPR and the administration of drugs such as epinephrine in connection with a search for and removal of reversible causes for the condition. Chest compressions and ventilation may extend the period of viability, although it is well known that standard CPR is a poor substitute for cardiac contractions. If cardiac output does not spontaneously return, death is probable. (Cripps, T and J Camm. The management of electromechanical dissociation. *Resuscitation.* 22(2): 173–180, 1991.) This may particularly be the case for patients with implantable automatic cardiovertor-defibrillators. The device may terminate an episode of ventricular fibrillation, cardiac electrical rhythm may be restored, and the patient may nevertheless die as a result of EMD. (Grubman, EM, et al. Cardiac death and stored electrograms in patients with third generation implantable cardiovertor defibrillators. *JACC.* 32(4): 1056–1062, 1998.)

The basic implantable cardiovertor/defibrillator system consists of at least one electrode attached to the heart and connected by a flexible lead to a shock or pulse generator. This generator is a combination of a power source and the microelectronics required for the system to perform its intended function. An implantable cardiovertor/defibrillator may also include a pacemaker to treat bradycardia. Many cardiovertor/defibrillators in current use incorporate circuits and antennae to communicate non-invasively with external instruments called programmers. Implantable cardiovertors/defibrillators have the capability of correcting dangerous tachyarrhythmias and fibrillation by applying selected stimulation patterns or high-energy shocks. High-energy shocks are used primarily to correct life-threatening tachyarrhythmias by essentially stopping the heart and allowing an appropriate rhythm to re-establish itself.

There remains a need, however, for apparatus that can not only terminate fibrillation, but can also identify post-defibrillation electromechanical dissociation, and provide a therapy.

It is an object of our invention, therefore, to provide a method for treating post-defibrillation electromechanical dissociation.

It is also an important object of our invention to provide an apparatus that can stimulate the heart in the presence of post-defibrillation EMD in such a manner as to restore life-sustaining cardiac output.

Another important object of our invention is to provide an implantable cardiovertor-defibrillator with apparatus for sensing and treating post-defibrillation EMD.

SUMMARY OF OUR INVENTION

We have invented an implantable defibrillator, which may include cardioversion and pace maker capabilities, which has the capability of detecting and treating post defibrillation EMD. The implantable defibrillator of our invention comprises a power source and microelectronic apparatus in a hermetically sealed case, and means for detecting and treating EMD.

The stimulator/defibrillator may be connected to the heart by one or more leads, the leads bearing electrodes. At least one electrode serves as an indifferent electrode, which electrode may be part of the hermetically sealed case. At least one electrode for defibrillaion is also provided. This electrode may be an endocardial or epicardial electrode or other suitable defibrillation electrode, as is known in the art. A sense circuit senses the electrical condition of the heart of the patient. A hemodynamic sensor is also provided for sensing a parameter correlated to the state of blood flow. The cardiac stimulator/defibrillator is capable of detecting ventricular tachyarrhythmia including fibrillation and providing a therapy to terminate ventricular tachyarrhythmia. After termination of the ventricular tachyarrhythmia, the stimulator/defibrillator can detect the presence of electrical rhythm in the heart correlated, however, with inadequate blood flow to sustain life (i.e., EMD). Under such conditions, the device provides an output to stimulate the heart to overcome electromechanical dissociation and restore adequate blood flow.

The device of our invention may also be used as an external therapy device, as part of, or in conjunction with an external defibrillator. We have also invented a method for treating the heart to restore blood flow where electromechanical dissociation occurs after termination of a ventricular tachyarrhythmia or ventricular fibrillation. The method comprises identifying electromechanical dissociation after termination of a ventricular tachyarrhythmia or a fibrillation and providing electrical therapy, the therapy comprising inducing or re-inducing ventricular fibrillation followed by delivery of defibrillating shocks.

We will now describe our preferred embodiment of our invention, in connection with the accompanying drawings.

DESCRIPTION OF OUR PREFERRED EMBODIMENT

We will now describe the preferred embodiments of the present invention in connection with the accompanying drawings. In the drawings like numerals are used to indicate like parts throughout. Our invention is described hereafter primarily in connection with an implantable cardiovertor/defibrillator, but an external, non-implantable device could also be used to implement the method of treatment described herein.

Figure 1:
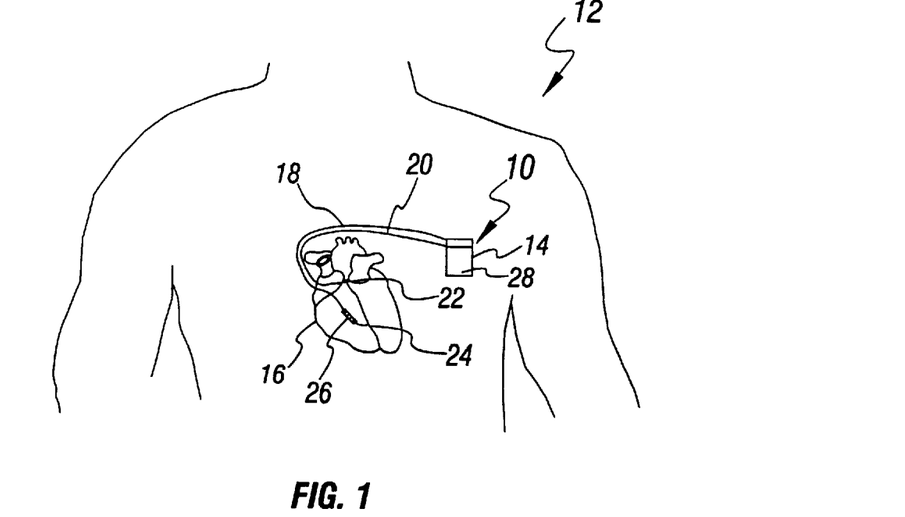
FIG. 1 is an illustration of an implantable pacemaker/defibrillator connected to the heart of the patient.

FIG. 1 represents an implantable cardiovertor/defibrillator 10 implanted in the body of a patient 12. The stimulator defibrillator 10 comprises a hermetically sealed can 14 containing electronic components and electrically connected to the heart 16 by a plurality of leads 18, 20. The leads 18, 20 have electrodes 22, 24, as is known in the art, for both stimulating and sensing the heart. A defibrillation electrode 26 is also provided. The defibrillation electrode 26 is illustrated as an endocardiai electrode, but epicardial patch electrodes and other forms of defibrillation electrodes are known in the art and could be used. An indifferent electrode 28 should also be provided. The indifferent electrode 28 may be a portion of the hermetically sealed case 14, or may be a separate electrode. For example, electrodes provided for so-called "bipolar" or "unipolar" pacing may be used as indifferent electrodes on the leads 18, 20 as a matter of design choice. Transvenous electrodes situated in, for example, the coronary venous system, such as posterior cardiac veins, may also be used.

Figure 2:
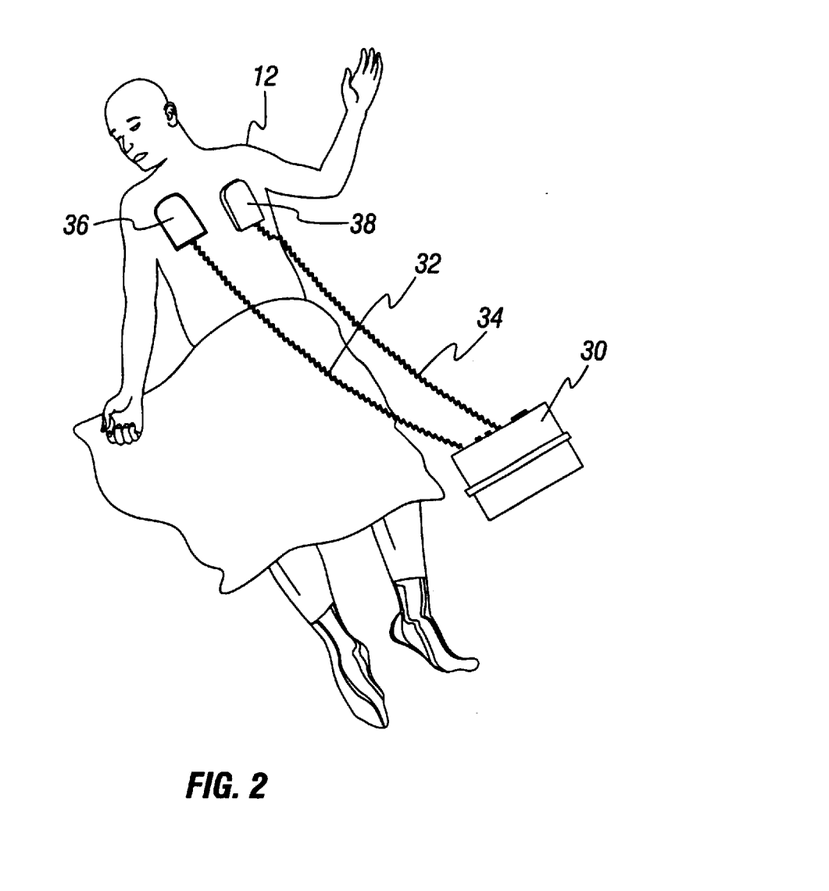
FIG. 2 is an illustration of an external stimulator connected to a patient.

The stimulator/defibrillator of our invention may also be used as an external device as illustrated in FIG. 2. In FIG. 2, an external apparatus 30 is illustrated connected to the patient 12 by leads 32, 34 and pad or patch electrodes 36, 38. Many configurations of suitable electrodes are known to those skilled in the art. Transcutaneous electrodes, as illustrated, may be employed, but subcutaneous electrodes, endoesophageal electrodes, or electrodes placed on the tongue or in the oral cavity or on the thorax or abdomen have also been suggested. Any suitable electrode configuration could be deployed with our invention.

Figure 3:
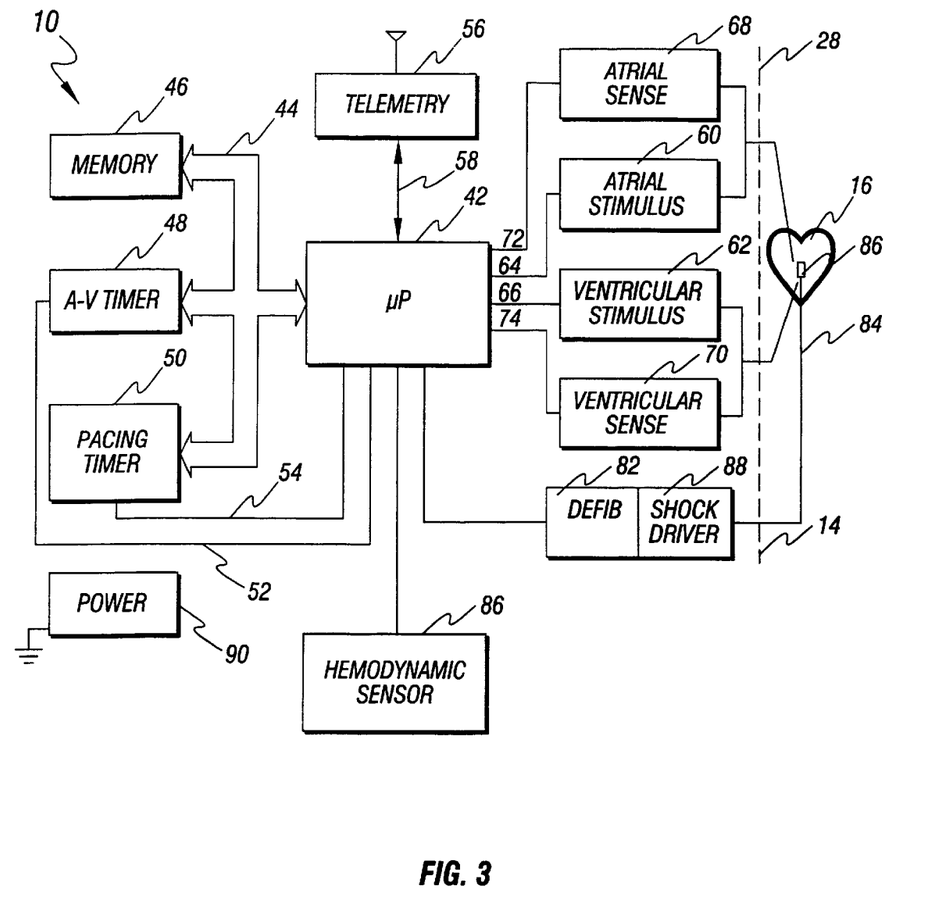
FIG. 3 is a block diagram of an implantable pacemaker/defibrillator.

FIG. 3 is a block diagram illustrating the pacemaker/defibrillator 10 according to our invention. A microprocessor 42 preferably provides pacemaker control and computational facilities, it will be appreciated that other forms of circuitry, such as analog or discrete digital circuitry, can be used in place of microprocessor 42. However, a microprocessor is preferred for its miniature size and its flexibility, both of which are important in the implantable systems in which it is envisioned the invention will find use. An energy efficient microprocessor which is designed specifically for use with implantable medical devices is fully described in Gordon, et al., U.S. Pat. No. 4,404,972, which is incorporated herein by reference.

The microprocessor 42 has input/output ports connected in a conventional manner via bi-directional bus 44 to a memory 46, an A-V interval timer 48, and a pacing interval timer 50. In addition, the A-V interval timer 48 and pacing interval timer 50 each has an output connected individually to a corresponding input port of the microprocessor 42 by lines 52 and 54 respectively.

Memory 46 preferably includes both ROM and RAM. The microprocessor 42 may also contain additional ROM and RAM as described in Gordon, et al., U.S. Pat. No. 4,404,972. The pacemaker operating routine is stored in ROM. The RAM stores various programmable parameters and variables.

The A-V and pacing interval timers 48, 50 may be external to the microprocessor 42, as illustrated, or internal thereto, as described in Gordon, et al. U.S. Pat. No. 4,404,972. The timers 48, 50 are suitable conventional up or down counters of the type that are initially loaded with a count value and count up to or down from the value and output a roll-over bit upon completing the programmed count. The initial count value is loaded into the timers 48, 50 on bus 44 and the respective roll-over bits are output to the microprocessor 42 on lines 52, 54.

The microprocessor 42 preferably also has an input/output port connected to a telemetry interface 56 by line 58. The defibillator, when implanted, is thus able to receive pacing, arrhythmia therapy, and rate control parameters from an external programmer and send data to an external receiver, if desired. Many suitable telemetry systems are known to those skilled in the art. One such system and encoding arrangement is described in Annstrong et al., U.S. Pat. No. 5,383,912 which is incorporated herein by reference.

The microprocessor output ports are connected to the inputs of an atrial stimulus pulse generator 60 and a ventricle stimulus pulse generator 62 by control lines 64 and 66 respectively. The microprocessor 42 transmits pulse parameter data, such as amplitude and width, as well as enable/disable and pulse initiation codes to the generators 60, 62 on the respective control lines. The microprocessor 42 also has input ports connected to outputs of an atrial sense amplifier 68 and a ventricular sense amplifier 70 by lines 72 and 74 respectively. The atrial and ventricular sense amplifiers 68, 70 detect electrical conditions in the heart including fibrillation and occurrences of P-waves and R-waves. The atrial sense amplifier 68 outputs a signal on line 72 to the microprocessor 42 when it detects a P-wave. The ventricular sense amplifier 70 outputs a signal on line 74 to the microprocessor 42 when it detects an R-wave.

The implantable cardiac stimulator 10 also has a defibrillator circuit 82. If fibrillation is detected through the ventricular sense amplifier 70 or as a consequence of antitachycardia therapy, a high-energy shock can be delivered through defibrillation lead 84 and electrode 86. An electric circuit through the heart is completed through the indifferent electrode 28, represented here as part of the can 14.

Detection algorithms for detection of tachycardias and fibrillation are described in Pless, et al., U.S. Pat. No. 4,880,005, incorporated herein by reference. Although an endocardial electrode and use of the conductive part of the can or case are suggested by the drawing, patch-type epicardial electrodes for defibrillation are also known. The shock is controlled by a shock driver circuit 88, which will be more particularly described hereafter.

A second sensor 86 is connected to the microprocessor 42. The second sensor 86 detects a parameter of the body correlated to blood flow. Numerous types of second sensors have been suggested. Impedance sensing has been used to detect the cardiac output of the heart. Pressure sensors, flow meters, Doppler flow sensors, ion transport sensors, oxygen, pH, piezoelectric and acoustic (acceleration or heart sound) sensors, among others, have been suggested, all of which detect parameters which can be correlated, more or less directly, to blood flow. For purposes of our invention, it is important to have a sensor, such as the ventricular sense amplifier 70, capable of detecting the electrical condition of the heart and a second independent sensor, such as the hemodynamic sensor 86, capable of detecting a physiological parameter correlated to blood flow. This sensor 86 may be located in the can 14, on or in the leads 18, 20, or may be placed in or near the patient's body 12.

All of the aforementioned components are powered by a power supply 90. The power supply 90 may comprise either standard or rechargeable batteries or both, which may be dedicated to the operation of different parts of the stimulator 10.

Figure 4:
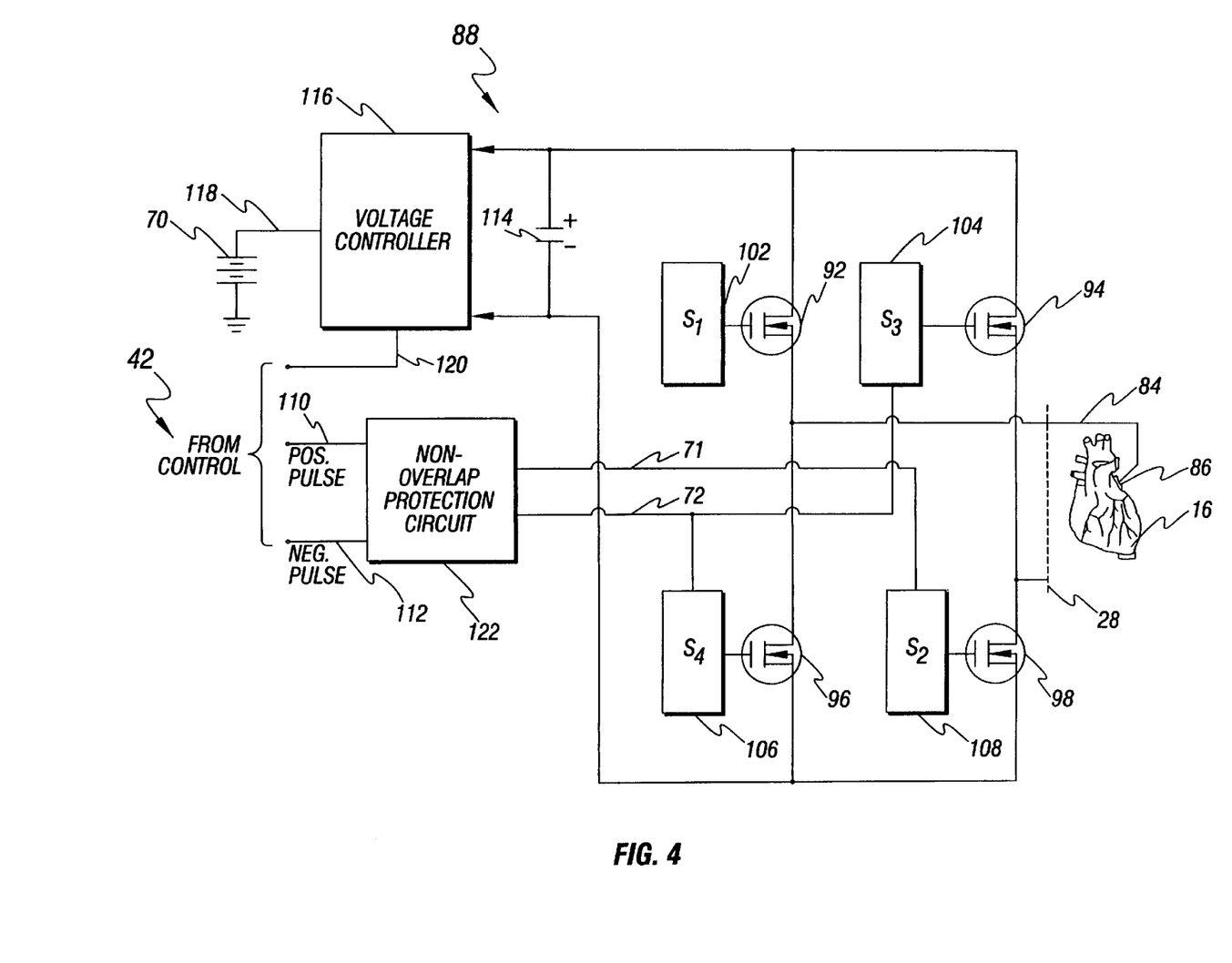
FIG. 4 is a block diagram of an output circuit for use in the defibrillator of FIG. 3.

In the preferred embodiment of our invention, we consider it desirable to produce multi-phasic shocks for defibrillation through the shock driver 88. Circuitry particularly well adapted for producing such waveforms is described in detail in U.S. Pat. No. 4,800,883 to Winstrom, the disclosure of which is incorporated herein by reference. Circuitry for the shock driver 88 is shown with greater particularity in FIG. 4. FIG. 4 illustrates the shock driver 88 connected to the patients heart 16 through the lead 84 and electrode 86 and through the indifferent electrode 28. To produce a biphasic waveform, a bank of four three-terminal semiconductor switches 92, 94, 96, 98, such as insulated gate bipolar transistor (IGBT) switches, may be employed. It will be understood, however, that our invention can be employed with monophasic pulse generators and with pulse generators incorporating multiphasic stimulation. The switches 92, 94, 96, 98 are controlled by drivers 102, 104, 106, 108 respectively. The drivers 102, 104, 106, 108 are controlled by command pulses from the microprocessor 42 through control lines 110 and 112, as will be more particularly described below. The energy to produce biphasic defibrillating shocks is supplied from high voltage capacitor 114. High voltage capacitor 114 is connected to switches 92 and 94, and current therefrom returns via switches 96 or 98. The lead 84 is connected between switches 92 and 96 while the indifferent electrode 28 is connected between switches 94 and 98.

The amount of energy delivered to the heart is dependent upon the voltage on the high voltage capacitor. The voltage appearing on the capacitor 114 is controlled by voltage controller 116, which is connected to a source of power such as the battery or power supply 70 through line 118. The voltage controller 116 is controlled through a line 120 from the microprocessor 42. This configuration is described in more detail in the Winstromm '883 patent mentioned above. In the configuration shown, to produce a unidirectional current pulse through the heart 16, the microprocessor 42 issues a command through a non-overlap protection circuit 122 to drivers 102 and 108, closing switches 92 and 98. Both before and after the command, all switches are normally opened. To produce an opposite current, the microprocessor 42 issues a command on line 124 to drivers 104 and 106, closing switches 94 and 96 and directing the current flow in the opposite direction through the heart 16.

Biphasic or monophasic electrical shocks may be delivered by this apparatus to terminate ventricular fibrillation. In addition, cardioverting therapies of lower voltage are known and applied to terminate ventricular tachyarrhythmias. See, for example, Pless, et al. U.S. Pat. No. 4,880,005 and Haluska, U.S. Pat. No. 5,002,052. Although cardioverting shocks may terminate the ventricular tachyarrhythmia, cardiac output is not restored in some patients, even though a recognizable and apparently adequate electrocardiogram is detected. This condition is called herein electromechanical dissociation (EMD), implying that the electrical condition of the heart is dissociated with the mechanical or pumping action of the organ. This condition is rapidly fatal if not corrected. The condition may also be referred to as pulseless electrical activity (PEA). For our purposes, both EMD and PEA are referred to as EMD. We have found that, after detection of electromechanical dissociation, re-inducing and then terminating fibrillation can be effective in restoring cardiac output. This is illustrated in the state transition diagram of FIG. 5.

Figure 5:
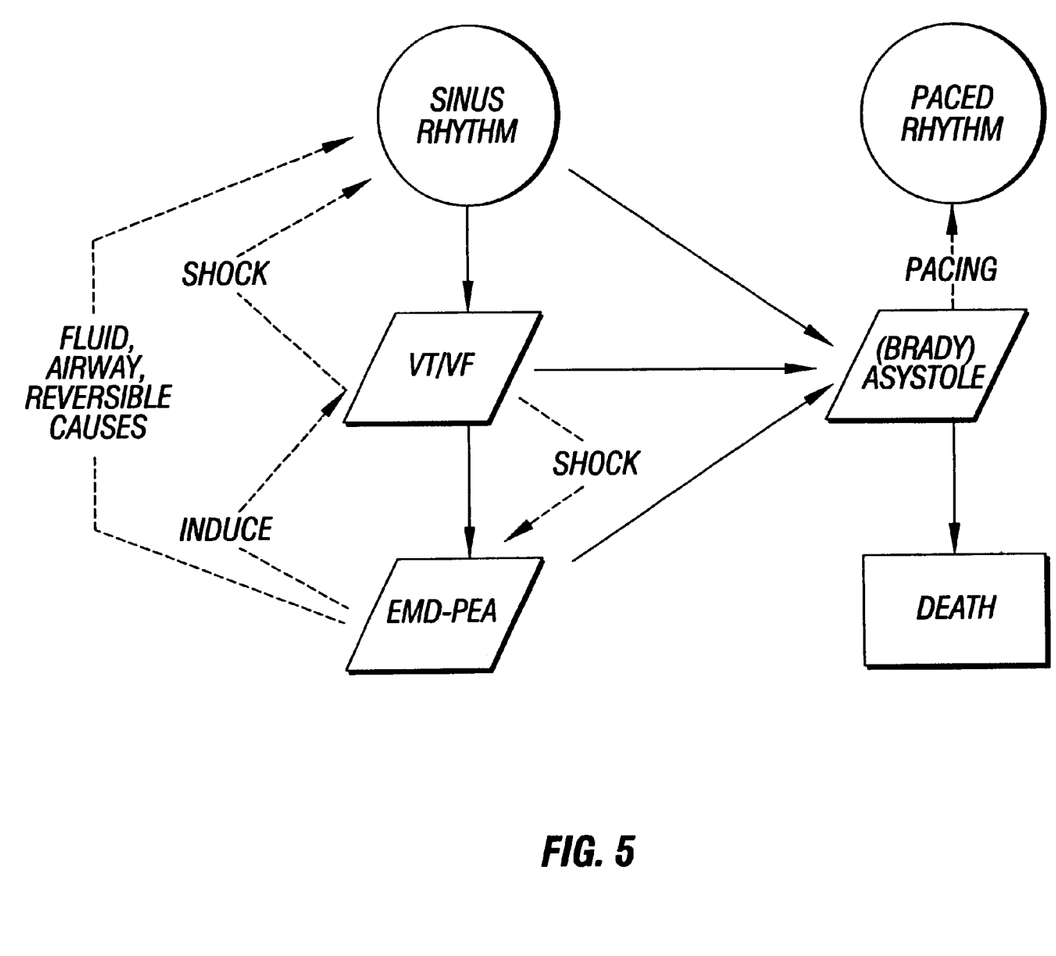
FIG. 5 is a state transition diagram illustrating the relationship of our EMD therapy to cardiac states.

The state transition diagram illustrates the two-step therapy for EMD. Spontaneous transitions from states are shown as solid lines and therapeutic interventions as dashed lines. Parallelograms identify transient physiological states. Ordinarily, a prompt defibrillating shock is sufficient to restore the heart's baseline rhythm from ventricular tachyarrhythmia or ventricular fibrillation. Occasionally, however, the resulting electrical rhythm appears sufficient for perfusion and recovery, but is not accompanied by detectable mechanical contractions, that is, the condition of EMD occurs. In the setting of sudden cardiac death, the interventions recommended in Advanced Cardiac Life Support (ACLS) training ("Textbook of Advanced Cardiac Life Support", American Heart Association, R. O. Cummins, ed. 1997) are rarely effective. Pericardiocentesis, for example, removes excess fluid from the pericardial sack surrounding the heart. if excess fluid is not a contributing factor causing the EMD, removing fluid will not terminate the EMD. The realization that EMD may occur after a therapeutic shock and that an appropriate response is induction of ventricular fibrillation followed by defibrillation shocks are important components of our invention.

Thus, among the most important observations of this invention is the recognition of ventricular fibrillation as, in some way not fully understood, a key intermediary state. In the absence of a treatable cause such as pericardial tamponade or hypovolemia, drugs and electrical therapies, such as pacing or shocks, have been ineffective. Mechanisms by which electrical activity can be uncoupled and recoupled to effective mechanical activity in the heart are poorly understood, but most explanations center around intracellular calcium ion storage, release, and uptake. It may be that a period of ventricular fibrillation, with its attendant multiple depolarizations, invokes interval-force associations like those of paired pacing and post extrasystolic potentiation.

Figure 6:
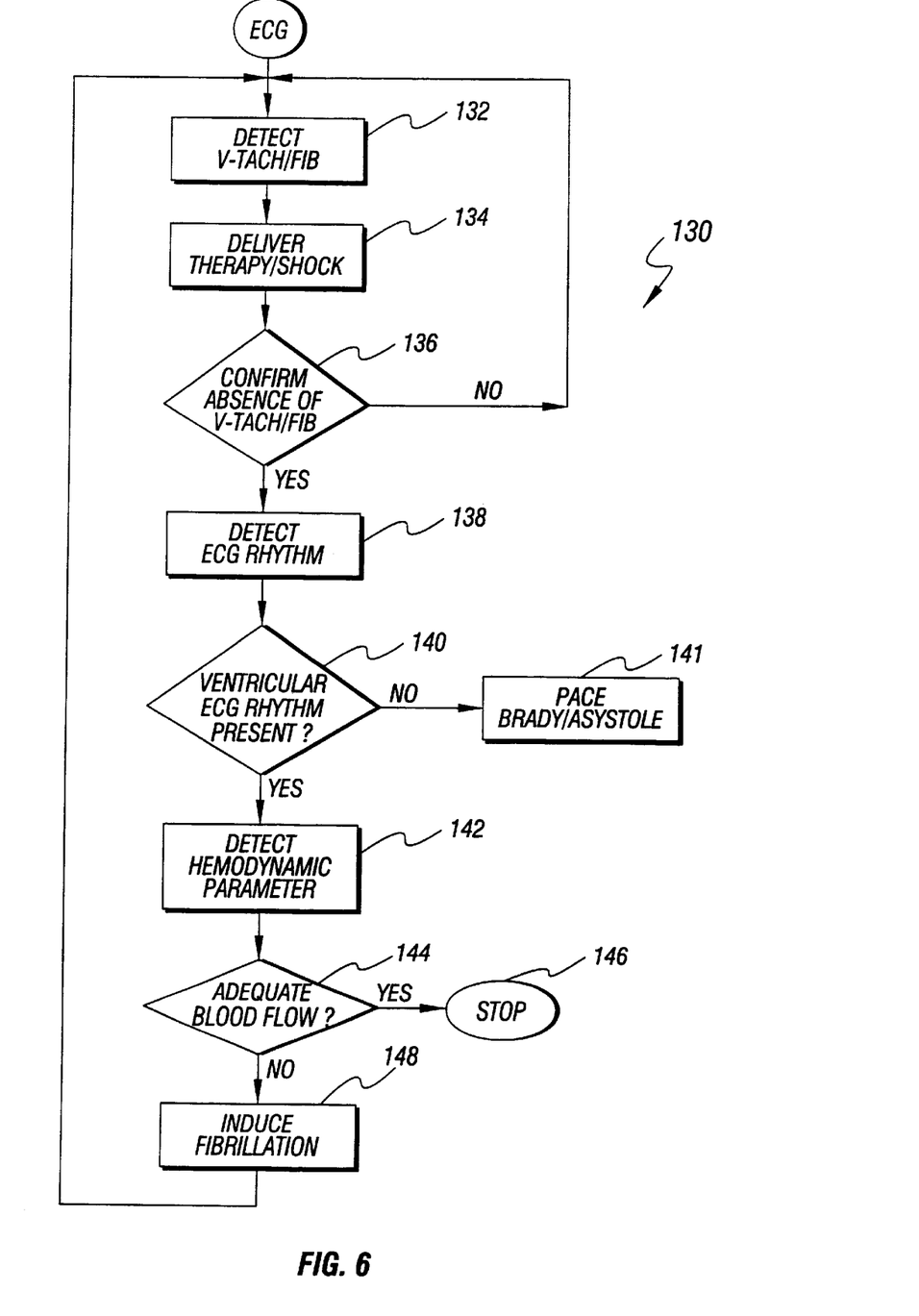
FIG. 6 is a flow chart for a program for producing the therapy according to our invention.

FIG. 6 illustrates an algorithm 130 for the termination of electromechanical dissociation following termination of a ventricular tachyarrhythmia including fibrillation. According to the algorithm 130, the stimulator/defibrillator 10 detects ventricular tachyarrhythmia or fibrillation 132 and delivers a therapy or shock 134. After delivery of the therapy, the absence of ventricular tachyarrhythmia or fibrillation is confirmed 136. The device then senses the ECG 138 through the ventricular sense amplifier 62 or a similar device. If the ECG is not present 140, pacing therapy for bradycardia or asystole may be applied 141. This therapy may be adjusted in accordance with known principles. See, e.g., Haluska, '052. If, on the other hand, the ECG is present, the device 10 will attempt to detect the hemodynamic parameter 142 through the hemodynamic sensor 86. If adequate blood flow is detected 144, the functioning of the heart has been restored and the algorithm can stop 146. If adequate blood flow is not detected, however, EMD is indicated, which must be treated.

We have discovered that, following termination of a ventricular tachyarrhythmia or fibrillation after which EMD occurs, EMD can be treated effectively by inducing or re-inducing ventricular fibrillation and re-applying defibrillation shock therapy. Although this may seem counterintuitive, we have been able to achieve resuscitations in canine models with this method.

Figure 7:
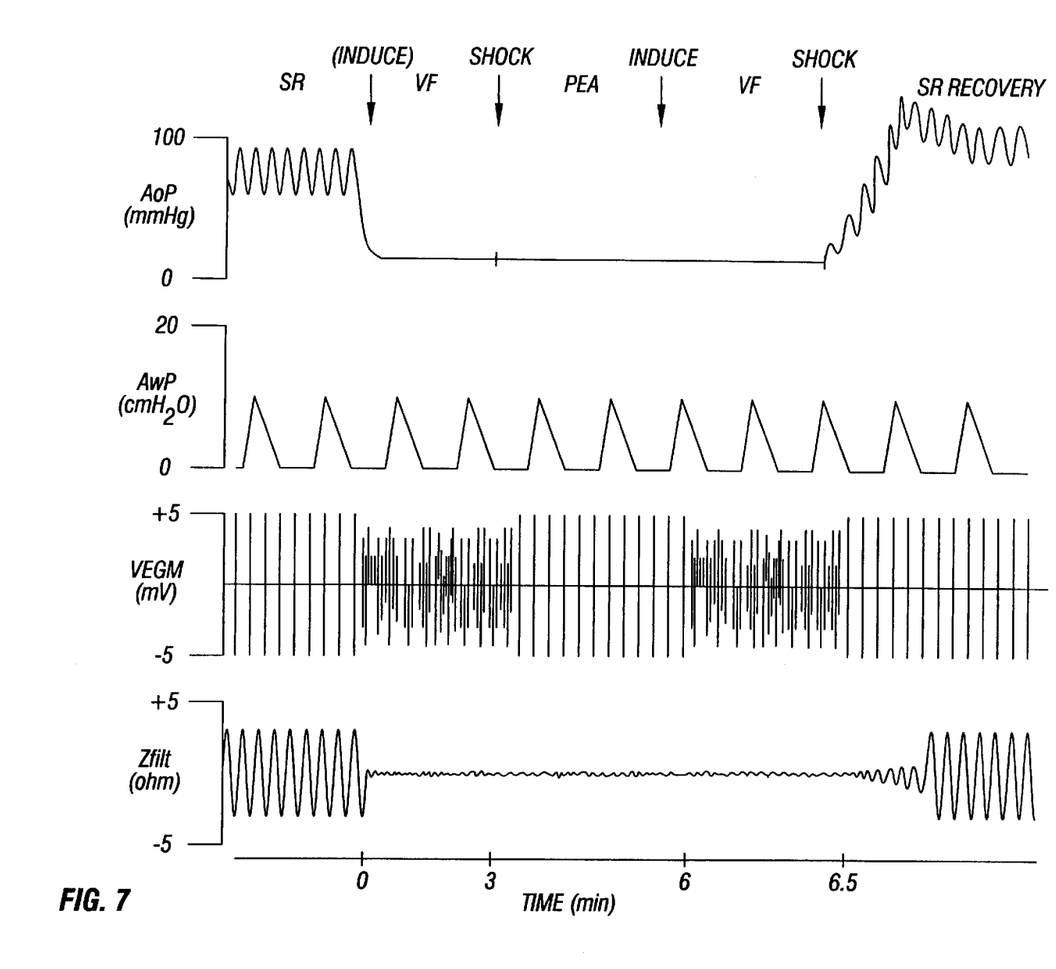
FIG. 7 is a schematic representation of an application of EMD therapy

FIG. 7 is a schematic diagram representing the sequence of events for recognition and therapy for EMD based on a canine study conducted November 26, 1996. From top to bottom, the signals represented are aortic blood pressure (AoP), airway pressure (AwP), ventricular endocardial electrogram (VEGM), and band pass filtered intracardiac impedance (Zfilt). In this instance, airway pressure (Awp) was maintained at a consistent rhythm by persistent mechanical ventilation. This record begins in sinus rhythm (SR) with good arterial blood pressure, normal ventricular electrical rhythm, and a normal cardiac impedance sensor signal. The onset of ventricular tachycardia/ventricular fibrillation (VT/VF) was artificially induced and is here shown to be accompanied by loss of perfusion pressure (AoP), a very rapid electrical rhythm (VEGM), and loss of organized or substantial mechanical contractions (Zfilt). Shock therapy, which ordinarily leads to a restoration of cardiac function, resulted in this case in EMD, which can be recognized by ACLS trained personnel or by an automatic external or implantable device by the relatively normal electrical rhythm conjoined with continued loss of second sensor amplitude. In this case, the second sensor was an impedance sensor for sensing mechanical hemodynamic response. Protection from sensor failure may be achieved by requiring the compete sequence of states from sinus rhythm (SR) to VT/VF to EMD be observed in the electrogram and sensor signals before EMD therapy is applied. EMD therapy comprises inducing (induce) ventricular fibrillation (VF) and delivering a shock (shock). Successful therapy results in restoration of a perfusing sinus rhythm (SR), as shown, indicated by a relatively normal electrical rhythm together with recovery of a relatively normal cardiac mechanical condition, detected by the second sensor. This condition could be detected by a device or by ACLS trained personnel. In the latter case, restoration of mechanical output of the heart would usually comprise detecting a palpable pulse.

Inducing or re-inducing fibrillation may be accomplished by several methods. Fibrillation is frequently induced during implantation of implantable cardiovertor—defibrillators in connection with establishing threshold shock energy levels for defibrillation. Among the methods available are the application of sinusoidal alternating current, usually at about 60 Hz or a pulsed approximation of such a current. Pacing-magnitude shocks, applied to fall within the "vulnerable" period of the T-wave of the cardiac cycle are also known to induce fibrillation in many cases. Many pacemakers, for example the Relay ™ pacemaker of Intermedics Inc., have provided noninvasive programmed stimulation or "NIPS" as a feature to allow physicians to evaluate electrophysiological variables. An unintended consequence of such investigation is the possibility of induction of arrhythmias requiring cardioversion or defibrillation, a known risk associated with electrophysiology testing. Use of the implanted device rather than an invasive procedure reduces the risks of infection, pneumothorax, vascular complications and patient discomfort. Attending physicians were nevertheless prepared for the possibility that fibrillation might occur. In this case, NIPS type stimulation may be used to intentionally re-introduce fibrillation in view of terminating EMD. NIPS type stimulation typically involves applying a selected number of pulses to the heart, usually between one and fifty. The pulses may be synchronized to a cardiac event, with a selected delay usually between 40 and 650 msec.

Once fibrillation has been re-introduced, the program 130 returns to the initial part of the program to test 132 for ventricular fibrillation. The program 130 then terminates fibrillation and resets for EMD. We have found that the heart may re-establish an effective pulse despite an earlier occurrence of EMD.

This therapy may also be employed in connection with other therapies such as chest compressions, cough CPR, oxygen, or epinephrine. Specific therapies for special conditions, such as hypoxia, hyperkalemia, hemorrhage, hypovolemia, hypercarbia, hypothermia, hypothyroidism, and cardiac tamponade, may also be instituted without interfering with the procedure described herein.

In the case of an automatic implantable cardiovertor-defibrillator employing the features of our invention, it may be desired to initiate a patient warning, such as a muscle-twitch stimulation or audible alarm, prior to initiating the re-fibrillation procedure. The patient or attending physician could then abort the procedure if the device had erroneously detected EMD. In addition, a sensor self-test may be initiated as part of step 144 prior to declaring a condition of inadequate blood flow. If the sensor failed to pass the self-test, inadequate blood flow would not be declared, thus preventing a sensor malfunction from being mistaken for EMD.

Figure 8:
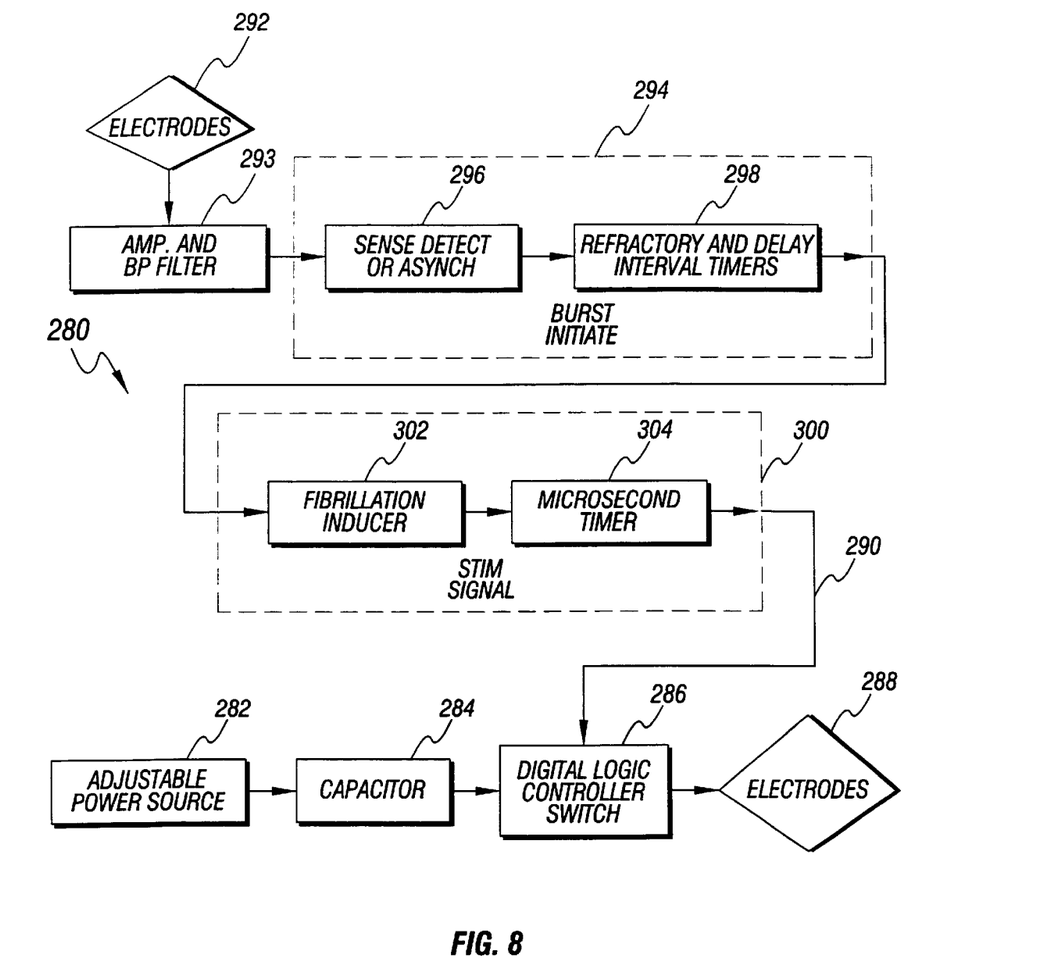
FIG. 8 is a block diagram of an external apparatus for use in our invention.

FIG. 8 illustrates, in block diagram, an external device used to produce and investigate the effectiveness of the therapy described herein. The external device 280 comprises an adjustable power supply 282 which supplies electrical power to a capacitor or capacitor bank 284. Energy stored in capacitor bank 284 is passed through a digital logic control switch 286 to electrodes 288. For purposes of testing, subcutaneous patch electrodes are employed, but many different electrode configurations could be used including surface electrodes or electrodes placed within the body cavities, within the venous system, or within the heart itself.

In the external apparatus 280, a signal is produced on line 290 to control the digital logic controlled switch 286. The signal on line 290 is initiated in response to sensed signals detected through electrodes 292 and band pass filter 293 for detecting a filtered ECG signal. As with the electrodes, which deliver therapy (which could be the same as the ECG detection electrodes), numerous different electrode configurations are known and could be employed to detect the ECG signal. A burst initiate block 294 begins the process of initiating the fibrillation induction treatment by receiving the ECG in a sense circuit 296, if it is desired to synchronize the therapy to a feature of the detected ECG signal. When the selected feature or level of ECG is detected, a refractory interval timer 298 times out a preselected period from the feature before initiated therapy. When the refractory interval timer times out, a simulation signal block 300 produces a set of control signals to initiate therapy. The stimulation signal block 300 comprises a fibrillation inducer 302 that triggers a selected pattern of pulses or current to induce fibrillation. A microsecond timer 304 controls the duration of pulses. The resulting control signal on line 290 controls the digital logic control switch 286 to produce the desired signal at the electrodes 288. As with the implantable device, an AC current, a digital approximation of an AC current, pacing stimuli coordinated with the T-wave, pacing stimulation in patterns similar to NIPS patterns, or other stimuli may be effective in inducing fibrillation.

Once fibrillation has been re-introduced, an external defibrillator, which may be a separate device or may be incorporated with the circuit described in connection with FIG. 8, may be employed to terminate the re-induced fibrillation. If the patient has an implanted automatic cardiovertor-defibrillator, re-induction of fibrillation will be effective to trigger the appropriate defibrillation response from the implantable cardiovertor-defibrillator. In any event, the patient must be monitored to confirm that EMD has not re-occurred following defibrillation.

While a preferred embodiment of our invention has been described above, it will be apparent to those skilled in the art from consideration of the disclosure herein that various modifications could be implemented without departing from the principles of our invention. Accordingly, it is intended that the scope of our invention be limited only by the appended claims.

What is claimed is:

1. An implantable cardiac stimulator/defibrillator comprising
   a hermetically sealed case;
   at least one lead having an electrode thereon, said electrode being electrically connected to said stimulator/defibrillator;
   an indifferent electrode electrically connected to said stimulator/defibrillator;
   a power source in said case;
   a control circuit connected to said power source;
   a sensor capable of sensing the electrical condition of the heart of a patient;
   a second sensor capable of sensing a parameter correlated to the state of blood flow;
   a correlation circuit associated with said control circuit capable of correlating a presence of electrical rhythm in the heart with an absence of a selected level of said parameter after an episode of tachyarrhythmia;
   an output circuit responsive to said correlation and control circuits, said output circuit producing an electrical output between said electrode and said indifferent electrode, said output being adapted to induce ventricular fibrillation,
   means for detecting ventricular fibrillation, and
   a circuit responsive to said means for detecting ventricular fibrillation, said circuit producing a defibrillation shock.

2. The implantable cardiac stimulator/defibrillator of claim 1 wherein said output circuit produces non-invasive programmed stimulation (NIPS).

3. The implantable cardiac stimulator/defibrillator of claim 1 wherein said output circuit produces an alternating electric current between at least two electrodes.

4. The impantable cardiac stimulator/defibrillator of claim 1 wherein said output circuit has a timer and delays application of fibrillation-inducing stimuli such that stimuli are likely to be delivered during the development of a T-wave in the ventricle of the heart.

5. The impantable cardiac stimulator/defibrillator of claim 1 wherein said output circuit produces unsynchronized shocks.

6. A cardiac stimulator comprising
   at least one lead having an electrode thereon, said electrode being electrically connected to said stimulator;
   an indifferent electrode electrically connected to said stimulator;
   a connection to a power source,
   a control circuit connected to said power source;
   a receiving circuit connected to said control circuit, said receiving circuit receiving instructions to initiate a therapy;
   an output circuit responsive to said receiving and control circuits, said output circuit producing an electrical output between said electrode and said indifferent electrode, said output being adapted to induce ventricular fibrillation, and
   a circuit for producing a defibrillation shock.

7. The implantable cardiac stimulator/defibrillator of claim 6 wherein said output circuit produces non-invasive programmed stimulation (NIPS).

8. The implantable cardiac stimulator/defibrillator of claim 6 wherein said output circuit produces an alternating electric current between at least two electrodes.

9. The impantable cardiac stimulator/defibrillator of claim 6 wherein said output circuit has a timer and delays application of fibrillation-inducing stimuli such that stimuli are likely to be delivered during the development of a T-wave in the ventricle of the heart.

10. The impantable cardiac stimulator/defibrillator of claim 6 wherein said output circuit produces unsynchronized shocks.

11. A method for treating a heart in electromechanical dissociation comprising the steps of
    identifying a dangerous tachyarrhythmia;
    applying a therapy to terminate said tachyarrhythmia;
    correlating an electrical rhythm in the heart after termination of said tachyarrhythmia with an absence of a selected level of cardiac output; and
    producing an output in response to said correlating of said electrical rhythm and said absence of said selected level of cardiac output to induce ventricular fibrillation, and
    producing a defibrillation shock.

12. The method of claim 11 wherein said output circuit produces non-invasive programmed stimulation (NIPS).

13. The method of claim 11 wherein said output circuit produces an alternating electric current between at least two electrodes.

14. The method of claim 11 wherein said output circuit has a timer and delays application of fibrillation-inducing stimuli such that stimuli are likely to be delivered during the development of a T-wave in the ventricle of the heart.

15. The method of claim 11 wherein said output circuit produces unsynchronized shocks.

16. An implantable cardiac stimulator/defibrillator comprising a control circuit;

a sensor capable of sensing the electrical condition of the heart of a patient;

a second sensor capable of sensing a parameter correlated to the state of blood flow;

a correlation circuit associated with said control circuit capable of correlating a presence of electrical rhythm in the heart with an absence of a selected level of said parameter after an episode of tachyarrhythmia;

an output circuit responsive to said correlation and control circuits, said output circuit producing an electrical output adapted to induce ventricular fibrillation, means for detecting ventricular fibrillation, and a circuit responsive to said means for detecting ventricular fibrillation, said circuit producing a defibrillation shock.

17. The implantable cardiac stimulator/defibrillator of claim 16 wherein said output circuit produces non-invasive programmed stimulation (NIPS).

18. The implantable cardiac stimulator/defibrillator of claim 16 wherein said output circuit produces an alternating electric current.

19. The implantable cardiac stimulator/defibrillator of claim 16 wherein said output circuit has a timer and delays application of fibrillation-inducing stimuli such that stimuli are likely to be delivered during the development of a T-wave in the ventricle of the heart.

20. The implantable cardiac stimulator/defibrillator of claim 16 wherein said output circuit produces unsynchronized shocks.

21. A cardiac stimulator comprising a control circuit;

a receiving circuit connected to said control circuit, said receiving circuit receiving instructions to initiate a therapy;

an output circuit responsive to said receiving and control circuits, said output circuit producing an electrical output between said electrode and said indifferent electrode, said output being adapted to induce ventricular fibrillation, and a circuit for producing a defibrillation shock.

22. The implantable cardiac stimulator/defibrillator of claim 21 wherein said output circuit produces non-invasive programmed stimulation (NIPS).

23. The implantable cardiac simulator/defibrillator of claim 21 wherein said output circuit produces an alternating electric current between at least two electrodes.

24. The implantable cardiac stimulator/defibrillator of claim 21 wherein said output circuit has a timer and delays application of fibrillation-inducing stimuli such that stimuli are likely to be delivered during the development of a T-wave in the ventricle of the heart.

25. The implantable cardiac stimulator/defibrillator of claim 21 wherein said output circuit produces unsynchronized shocks.

26. An implantable cardiac stimulator/defibrillator comprising a control circuit;

a sensor capable of sensing the electrical condition of the heart of a patient;

a second sensor capable of sensing a parameter correlated to the state of blood flow;

a correlation circuit correlating a presence of electrical rhythm in the heart with an absence of a selected level of said parameter;

an output circuit producing an electrical adapted to induce ventricular fibrillation, a ventricular fibrillation detector, and a defibrillation shock circuit responsive to said detector.

27. The implantable cardiac stimulator/defibrillator of claim 26 wherein said output circuit produces non-invasive programmed stimulation (NIPS).

28. The implantable cardiac stimulator/defibrillator of claim 26 wherein said output circuit produces an alternating electric current between at least two electrodes.

29. The impantable cardiac stimulator/defibrillator of claim 26 wherein said output circuit has a timer and delays application of fibrillation-inducing stimuli such that stimuli are likely to be delivered during the development of a T-wave in the ventricle of the heart.

30. The impantable cardiac stimulator/defibrillator of claim 26 wherein said output circuit produces unsynchronized shocks.

31. A cardiac stimulator comprising an output circuit producing an electrical output to induce ventricular fibrillation, and a circuit for producing a defibrillation shock.

32. The implantable cardiac stimulator/defibrillator of claim 31 wherein said output circuit produces non-invasive programmed stimulation (NIPS).

33. The implantable cardiac stimulator/defibrillator of claim 31 wherein said output circuit produces an alternating electric current between at least two electrodes.

34. The impantable cardiac stimulator/defibrillator of claim 31 wherein said output circuit has a timer and delays application of fibrillation-inducing stimuli such that stimuli are likely to be delivered during the development of a T-wave in the ventricle of the heart.

35. The impantable cardiac stimulator/defibrillator of claim 31 wherein said output circuit produces unsynchronized shocks.

36. A method for treating a heart in electromechanical dissociation comprising the steps of identifying electromechanical dissociation in a patient;

applying an electrical output to the body of said patient to induce ventricular fibrillation, identifying fibrillation in said patient; and applying a defibrillation shock to the body of said patient.

* * * * *

UNITED STATES PATENT AND TRADEMARK OFFICE
CERTIFICATE OF CORRECTION

PATENT NO.    : 6,298,267 B1
DATED         : October 2, 2001
INVENTOR(S)   : Rosborough et al.

It is certified that error appears in the above-identified patent and that said Letters Patent is hereby corrected as shown below:

Column 1,
Line 12, delete "postdefibrillation" and insert -- post-defibrillation --, therefor.

Column 3,
Line 31, after "therapy" insert -- . --, therefor.
Line 54, delete "endocardiai" and insert -- endocardial --, therefor.

Column 4,
Line 53, delete "Annstrong et al." and insert -- Armstrong et al. --, therefor.

Column 6,
Line 8, delete "Winstromm" and insert -- Winstrom `833 patent --, therefor.

Column 8,
Line 31, delete "resests" and insert -- re-tests --, therefor.

Column 10,
Lines 11, 16, 42 and 47, delete "impantable" and insert -- implantable --, therefor.

Column 12,
Line 15, delete "electrical adapted" and insert -- electrical output adapted --, therefor.
Lines 25, 30, 44 and 48 delete "impantable" and insert -- implantable --, therefor.

Signed and Sealed this

First Day of October, 2002

Attest:

JAMES E. ROGAN
Attesting Officer       Director of the United States Patent and Trademark Office